United States Patent [19]

Bryenton et al.

[11] Patent Number: 5,134,281
[45] Date of Patent: Jul. 28, 1992

[54] MICROBEND OPTIC SENSOR WITH FIBER BEING SEWN THERETO IN A SINUOUSLY LOOPED DISPOSITION

[75] Inventors: Earl L. Bryenton; Frank Johnson, both of Ottawa; Menno Stoffels, Nepean; Alan L. Bryenton, Ottawa, all of Canada

[73] Assignee: E.L. Bryenton & Associates Inc., Nepean, Canada

[21] Appl. No.: 631,871

[22] Filed: Dec. 21, 1990

[30] Foreign Application Priority Data

Jan. 31, 1990 [CA] Canada .................................. 2009033

[51] Int. Cl.⁵ .............................................. H01J 40/14
[52] Int. Cl. ............................. 250/227.16; 250/227.14
[58] Field of Search ....................... 250/227.16, 227.14, 250/227.24, 229, 231.1, 231.19; 128/748, 675; 73/705

[56] References Cited

U.S. PATENT DOCUMENTS

| | | |
|---|---|---|
| 3,789,667 | 2/1974 | Porter et al. ............................. 73/705 |
| 4,691,708 | 9/1987 | Kane ....................................... 73/705 |
| 4,692,610 | 9/1987 | Szuchy ............................ 250/227.14 |
| 4,745,925 | 5/1988 | Dietz ....................................... 73/705 |
| 4,937,444 | 6/1990 | Zimmerman .................... 250/231.1 |
| 4,972,074 | 11/1990 | Wright ............................ 250/227.24 |
| 4,991,590 | 2/1991 | Shi ......................................... 73/705 |

Primary Examiner—David C. Nelms
Assistant Examiner—Que T. Le
Attorney, Agent, or Firm—Pascal & Associates

[57] ABSTRACT

An optical sensor comprising an optical fiber having a core covered by a cladding, the cladding having an index of refraction different from that of the core, apparatus for retaining the fiber in a sinuously looped disposition, apparatus for fixing the fiber to an object to be sensed whereby movement to be sensed results in one or both of accordion expansion and contraction of loops of the fiber and microbending of the fiber, apparatus for applying a first optical signal into one end of the fiber, apparatus for detecting a resulting optical signal from the other end of the fiber, and apparatus for comparing the first and resulting optical signals to obtain an indication of the movement.

7 Claims, 3 Drawing Sheets

MICROBEND OPTIC SENSOR WITH FIBER BEING SEWN THERETO IN A SINUOUSLY LOOPED DISPOSITION

BACKGROUND OF THE INVENTION

This invention relates to a sensor which uses an optical fiber for monitoring relative movements such as physiological activity, vibrations or movement of structures and apparatus where a strain gauge or displacement monitor would otherwise be used.

Strain gauges are usually used to monitor warning or destructive movements of various structures, such as pipelines, bridges, buildings, etc., or to monitor earth movements. Myoelectric potential detecting devices are sometimes used for physiological sensing, e.g. for monitoring heart beat or other muscle movements. The presence of breathing has been monitored using sound or air pressure sensors attached to the nostrils. Such physiological sensors require electrical connection to the skin, or are otherwise uncomfortable or painful to the patient.

The present invention is a transducer for monitoring vital signs of persons, animals, etc. using a comfortable to use structure. The invention can be adapted to detect non-physiological displacements, such as the movement of buildings, structures, etc. including machinery, bridges, earthquakes, blasts, for security and intrusion alarms, etc., e.g. wherever a strain gauge or displacement transducer can be used.

The present invention uses an optical fiber in a particular form as a strain sensor using the phenomenon of microbending, as will be described below:

DESCRIPTION OF THE PRIOR ART

U.S. Pat. No. 4,654,520 which issued Mar. 31, 1987 to Richard W. Griffiths describes the use of an optical fiber as a strain gauge. The fiber is fixed to a pipe or another object to be monitored at two or more points. When the pipe or other object bends, the transmission characteristics of the light signal through the optical fiber change, and are detected. The patent points out that the effect can be enhanced by the use of the particular phenomenon of microbending. In microbending the refractive index of an optical fiber cladding is changed to a value close to or equal to that of the core by bending of the fiber, and as a result, light that would otherwise be internally reflected at the interface of the core and the cladding partly escapes into the cladding.

Griffiths states that greatly increased sensitivity can be obtained using an integral continuum of microbend elements.

U.S. Pat. No. 4,675,521 issued June 23, 1987 to Hiroshi Sugimoto uses what appears to be microbending. In this case the cladding of a fiber optic cable is pinched or depressed by a contact member, causing the escape of optical signals from a fiber optic core.

In both of the aforenoted patents, variation of the amplitude of the light signal passing through the optic fiber and changed by an external force is measured. In both cases it is the bending of the straight segment of fiber which causes the effect to be measured.

The microbending fiber optic transducers described in the aforenoted two patents are not suitable for use as physiological monitors for several reasons. For example, where the chest expansion and contraction of a baby is to be monitored, wrapping the optical fiber around the baby's chest would constrict the breathing, causing distress. Secondly, there is no evident way to cause the bending after wrapping the optical fiber around a significant portion of the body since the body would be in effect bound up. There is also no evident way of monitoring delicate movements of part of the chest wall which is required in order to monitor heart beat.

SUMMARY OF THE INVENTION

The present invention is an optical sensor which uses exclusively the microbending phenomenon in an optical fiber structure which is ideally suited for the aforenoted physiological monitoring. The invention is made possible by a unique structure, and also the discovery that one can obtain a high change in the microbending loss in the fiber, and thus high sensitivity, if the fiber is bent into one or more loops each having a particular maximum smallest radius for a given fiber diameter. This is achieved by creating an optical fiber which is sinuously looped, and which is disposed on a mount which allows the fiber to expand its loops like the bellows of an accordion with physiological movement of the person or animal or part thereof which is monitored. This allows expansion and contraction of the transducer, while utilizing the microbending phenomenon, which is not possible using the aforenoted prior art fiber structures. As a result the present invention can be used as a physiological monitor, worn on or around the body or over the part of the body to be monitored without invasion of the body, and without pain or discomfort, while being highly effective.

With the extremely high sensitivity obtained due to the presence of the multiple loops in the structure, small physiological movements such as heart beats can be sensed, while larger movements such as expansion and contraction of the chest resulting from breathing can as well be sensed. The invention may be used to monitor limb volume during plethysmography. The signal from the device is linearly related to the strain applied to limbs measured, while blood or fluid is being drained. The invention can also be used to monitor penile tumescence, without the need for bulky or harmful sensors.

The transducer can also be used to monitor movement of machinery relative to a fixed point, parts of the machinery relative to other parts, the motion of structures relative to a suspended relatively massive weight, expansion or contraction of devices such as electronic or other substrates, e.g. caused by temperature or pressure variation, movements of parts of buildings, bridges caused by various phenomenon such as blasts, earthquakes, etc. An example is a large scale vibration detector for intrusion alarm or sound detection. Acoustic pressure waves may be detected using an appropriate diaphragm. Indeed, the sensitivity of the sensor can be tailored to the application by providing more or fewer loops, even as few as one loop.

A preferred embodiment of the invention is an optical sensor comprising an optical fiber comprised of a core covered by a cladding, the cladding having an index of refraction different from that of the core, apparatus for retaining the fiber in a sinuously looped disposition, apparatus for fixing the fiber to an object to be sensed whereby movement to be sensed results in one or both of accordion expansion and contraction of the fiber, apparatus for applying a first optical signal into one end of the fiber, apparatus for detecting a resulting optical signal from the fiber, and apparatus for comparing the first and resulting optical signals to obtain an indication of the movement.

BRIEF INTRODUCTION TO THE DRAWINGS

A better understanding of the invention will be obtained by reference to the detailed description below, with reference to the following drawings, in which:

FIG. 1 illustrates a segment of a loop of optical fiber,

FIG. 2 is a schematic illustration of a first embodiment of the present invention, FIG. 3 is a schematic illustration of a second embodiment of the present invention, FIG. 4 is a block diagram of the electronic processor portion of FIG. 3, which can be used also with the embodiment shown in FIG. 2, FIG. 5 is another embodiment of the invention, FIG. 6 is a schematic view of the present invention in the form of a microphone, and FIG. 7 is a plan view of a room illustrating the present invention in the form of an intrusion detector.

DETAILED DESCRIPTION OF THE INVENTION

Figure 1:
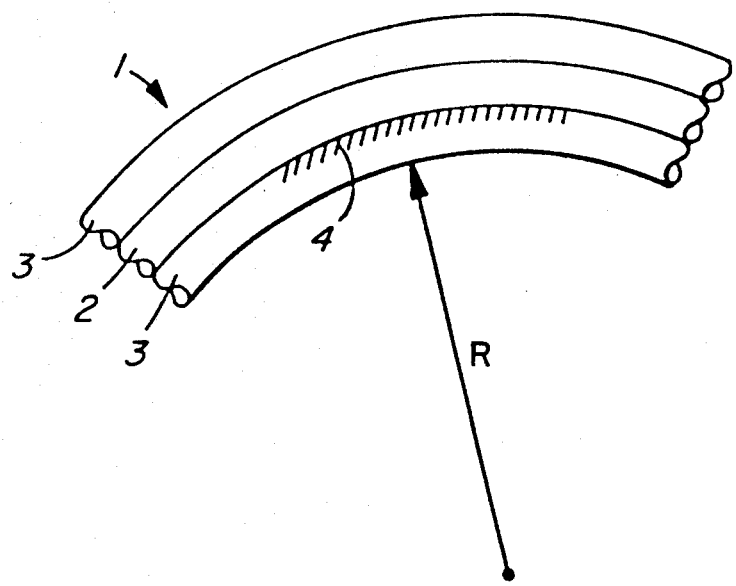

FIG. 1 illustrates a portion of a looped optical fiber which utilizes microbending. The loop is fixed to a resilient or expandable backing, and has a maximum smallest radius R. The radius should be selected to obtain significant microbending optical loss when the loop is strained by bending so that the radius increases or decreases. For example, if the optical fiber has a 125 micron diameter, the maximum smallest radius of the bend should be not more than about 4 mm. Where the optical fiber is 250 microns, the maximum smallest radius of the bend should be not more than about 8 mm.

The fiber 1 is formed of a core 2 surrounded by a cladding 3. The cladding should have an index of refraction which is different, preferably larger, from that of the core. When the fiber bends, changing the radius R, the cladding is stressed, e.g. at the cross hatched portion referenced 4. The portion of the cladding opposite that reference 4 is also stressed. The result is variation of the index of refraction of the cladding at one or the other sides of the core, so that it closely approaches or becomes equal to the index of refraction to the core 2. The result is loss into the cladding of light energy passing through from one end of the core 2 which would otherwise be totally internally reflected. The loss of light from the core or its change can be sensed at the other end of the core, and can be characterized as a variation of the impedance of the fiber.

As the loop is flexed and the radius R of the loop becomes smaller and larger, this change in impedance can be monitored, and results in a signal which is related to the change in radius R.

Figure 2:
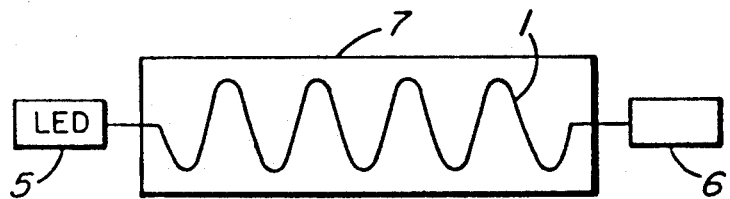

FIG. 2 illustrates an embodiment of the invention. The fiber 1 is retained preferably in a sinuously looped disposition. Each of the loops has a radius of approximately R as described with reference to FIG. 1. The fiber has a light source 5, such as a light emitting diode LED connected at one end thereof in order to apply light energy down the core of the optical fiber. A light sensor 6 is connected to the opposite end of the core of the fiber 1.

The fiber is fixed in order to hold its general shape when not stressed, to an expandable backing 7. In one successful embodiment of the invention, the flexible backing 7 was formed of elasticized cloth, and the fiber was sewn thereto in its sinuous disposition.

In operation of a successful prototype, the backing 7 was disposed over the chest of an infant whose breathing was to be monitored and tied around its body. A light was applied via LED 5 and was sensed at light sensor 6. Breathing of the infant caused expansion of the backing 7, causing the loops of fiber 1 to expand and contract like the bellows of an accordion. This caused increase and decrease of the radii R, and through the phenomenon of microbending, loss and variation of loss of light into the cladding in a rhythmic manner with the breathing of the infant and expansion and contraction of the backing 7.

Inspiration by the infant caused expansion of the backing 7 and increase of the radii R. Expiration of the infant caused contraction of the backing 7 and decrease of the radii R. As a result an electronic processor receiving the light signal provided a record of the breathing of the infant.

The processor could also detect the absence of variation of light, i.e. absence of breathing over a predetermined time period, and should apnea exist, operate an alarm.

A structure similar to that shown in FIG. 2 made smaller and having increased sensitivity by using a large number of loops, taped at its ends to the chest of an infant over the heart, was able to monitor heart beat.

With physiological vital sign sensing of an infant using the structure described above, serious problems such as sudden infant death syndrome would in many cases be able to be averted. The invention has particular application to infants that are predisposed to occurrence of sudden infant death syndrome.

Figure 3:
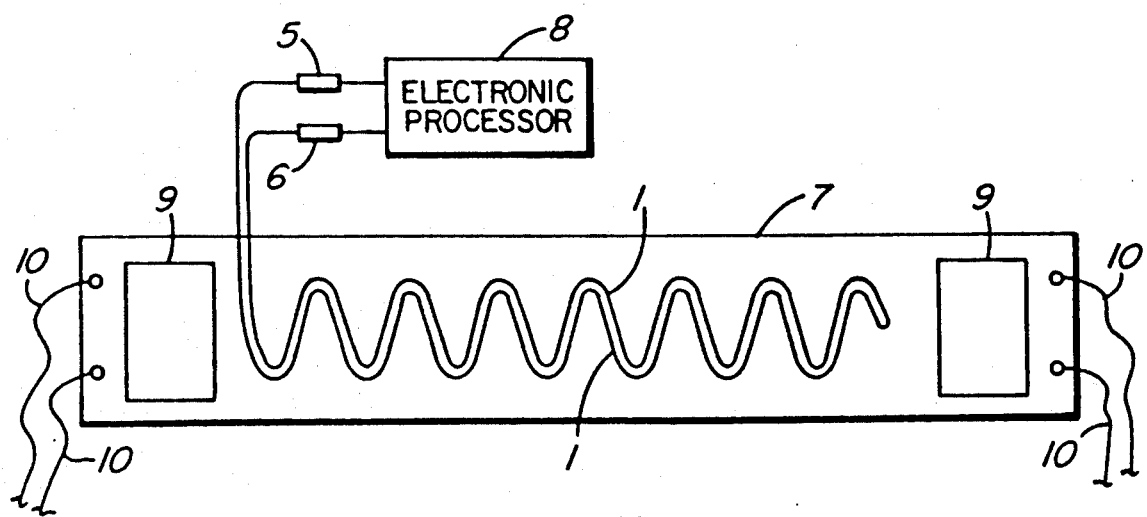

FIG. 3 illustrates another embodiment of the invention. In this case the fiber 1 is looped in a sinuous manner and is retained on an expandable backing 7, but is looped back upon itself along the same path. This structure provides two additional benefits over that shown in FIG. 2. Because there are double the number of loops traversing a given length of backing 7, the amount of attenuation for a certain expansion of the backing 7 can be doubled, resulting in increased sensitivity.

Secondly, the LED and sensor 5 and 6 can be brought to a single connection point and connected via a double connector to an electronic processor 8.

The embodiment shown in FIG. 3 illustrates two additional features that can be used. The ends of the backing 7 contain pads 9 of Velcro TM. With this structure the invention can be removable from a sensor harness that may be attached to a patient, and can be removed during e.g.. waking hours and reapplied during sleeping hours. It also allows the transducer to be fixed to corresponding pads on an article of machinery or the like as described earlier, and to be removed easily.

The transducer can have laces, Velcro TM 10 or a similar fastener fixed to the ends thereof for fixing around the body of a person to be monitored.

Figure 4:
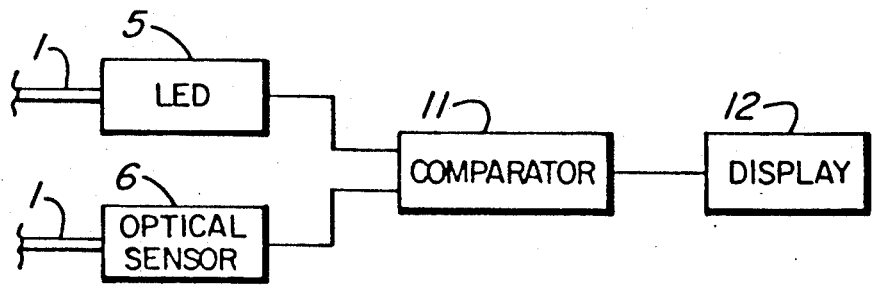

Turning to FIG. 4, a block diagram of an electronic processor 8 is illustrated. LED 5 which applies light energy to the core of optical fiber 1 has its electrical input connected to one input of comparator 11. Optical sensor 6 has its electrical output connected to the other input of comparator 11. Comparator 11 provides a signal formed of the difference between the two signals to display 12. If there is no variation in the radius R of the loop, the signals applied to comparator 11 will be virtually identical, assuming little or no loss in the optical fiber. The display, which can be an oscilloscope, printer, alarm, strip chart, or other corresponding device, will provide the appropriate output.

With variation in the radius R of the loops, there will be optical signal loss in the fiber, and there will be a difference signal output from comparator 11 to display 12.

Should the transducer be monitoring the breathing of an infant, for example, the result on display 12 will be a sinuous line representing expansion and contraction of the chest of the infant. Should breathing stop, the line will be horizontal at a low level. Should this occur, an ancillary alarm can be used to alert medical personnel that breathing has stopped, e.g.. after a timeout.

Figure 5:
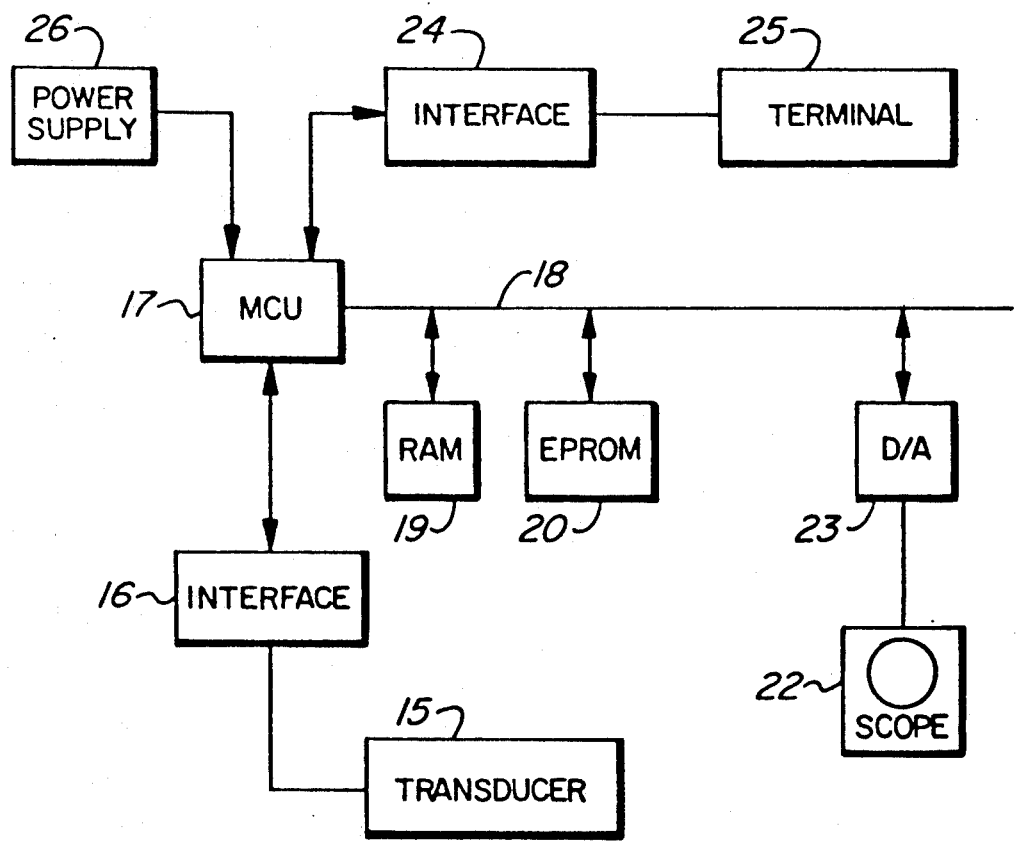

FIG. 5 illustrates another embodiment of the invention. Transducer 15 represents the structure comprising the sinuously looped fiber and expandable backing, LED 5 and optical sensor 6. Interface 16 represents an analog to digital converter. MCU 17 is a microcomputer unit. A bus 18 is connected to the microcomputer unit 17, and random access memory RAM 19 and erasable programmable read only memory EPROM 20 are connected to the bus 18. An oscilloscope 22 is connected via a digital to analog converter 23 to the bus 18. The microcomputer unit 17 is also connected to an interface 24 for connection to a user terminal 25, via typically an RS232 port. A power supply 26 is connected to the microcomputer unit.

The microcomputer unit 17 operating by means of programs stored in RAM 19, causes application through interface 16 of an optical signal to transducer 15, and receives the resulting signal via interface 16. It performs a comparator function, and causes display of the result on oscilloscope 22 via digital to analog converter 23, the latter converting the digital signals from MCU 17 into analog signals used by oscilloscope 22.

The MCU 17 can be controlled from terminal 25 through interface 24.

The aforenoted display functions can thereby be generated, and if desired, alarm signals additionally generated. Further, a record of the results can be stored in memory or on a disk storage memory (not shown), and various cycles of physiological variation can be compared one with the other, or grouped.

Figure 6:
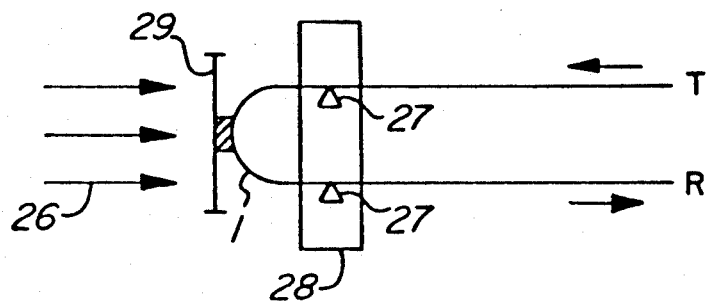

FIG. 6 illustrates the invention forming a microphone. An optical fiber loop of the type described above is fixed at positions 27 to a support 28, so that the loop can flex, changing its radius, under external pressure. A diaphragm 29 is fixed from its center point to the loop of the fiber 1, the diaphragm being located so as to receive sound or ultrasonic waves 26. A light signal such as described above is applied to one end T of the core of the fiber, while the resulting light signal is received at the other end, R. The resulting light signal is modulated with the sound or ultrasonic waves, which can be detected by demodulation.

Figure 7:
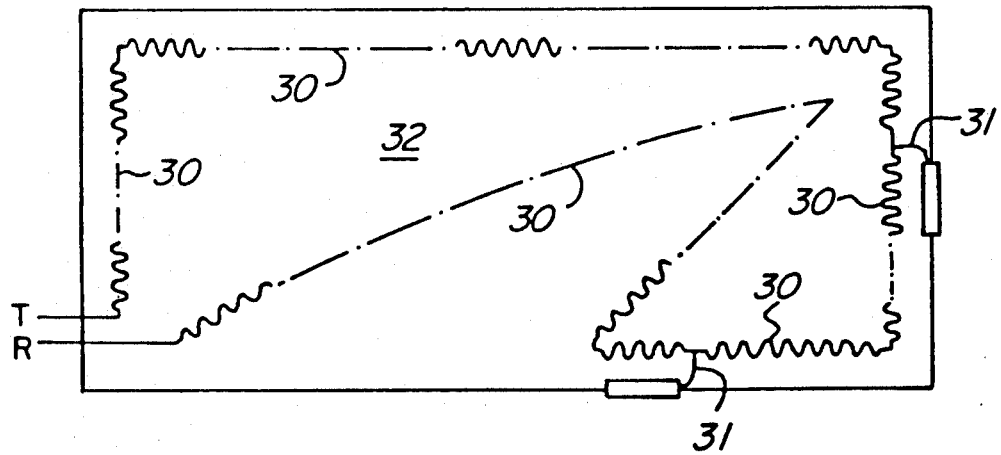

FIG. 7 illustrates in a plan view of a room 32 the invention forming an intrusion detector. Sensor lengths 30 of multiple loop optical fiber, retained to a backing in a manner described earlier, are located around a room to be protected, and are connected in series, with a length or lengths preferably hidden, running under a floor covering where an intruder would step. Preferably the length of each sensor is at least 20 times the physical amplitude of the loops. Attachments 31 to windows, doors, etc. are made from the sensors so that should a door or window be moved, the fiber will be microbent, resulting in detection using the system described earlier with respect to FIGS. 4 and 5. Similarly, the fiber will be microbent under pressure from floor covering that is stepped on. In this manner, a person intruding into the room by door or window, or stepping on the floor covering over a sensor, will be detected.

It should be noted that the sensor can be made in various forms, such as the forms described above, or in the form of a belt, netting, etc. Rather than being sinuously looped, the fiber can be looped in a circle or oval. It can be made in various sizes and with different numbers of loops for various applications. A single sensor can have loops having various loop radius to provide variations in sensitivity for different bending increments.

A person understanding this invention may now conceive of other embodiments or variations in design using the principles disclosed herein. All are considered to be within the sphere and scope of this invention as defined in the claims appended hereto.

We claim:

1. An optical sensor comprising an optical fiber having a core covered by a cladding, the cladding having an index of refraction different from that of the core, means for retaining the fiber in a sinuously looped disposition, means for fixing the fiber and retaining means to an object to be sensed whereby movement to be sensed results in one or both of accordion expansion and contraction of loops of the fiber and microbending of the fiber, the retaining means being comprised of an elastic cloth strip, the fiber being sewn thereto in said sinuously looped disposition, means for applying a first optical signal into one end of the fiber, means for detecting a resulting optical signal from he other end of the fiber, means for comparing the first and resulting optical signals to obtain an indication of said movement, the fiber being loped back upon itself so as to form a first portion and a looped-back portion, both portions of the fiber being disposed so as to follow the same path.

2. An optical fiber as defined in claim 1 in which loops have predetermined maximum smallest radius relative to the fiber diameter which are sufficiently small so as to obtain significant microbending loss thereat.

3. An optical sensor as defined in claim 1 in which the fiber has a diameter of about 100 microns, and the radius of each loop is no greater than about 4 mm.

4. An optical sensor as defined in claim 2 in which the fiber has a diameter of about 250 microns, and the radius of each loop is no greater than about 8 mm.

5. An optical sensor as defined in claim 1 in the form of a belt.

6. An optical sensor as defined in claim 1 having a length at least 20 times the physical amplitude of the loops.

7. An optical sensor comprising an optical fiber having a core covered by a cladding, the cladding having an index of refraction different from that of the core, means for retaining the fiber in a sinuously looped disposition, means for fixing the fiber and retaining means to an object to be sensed whereby movement to be sensed results in one or both of accordion expansion and contraction of loops of the fiber and microbending of the fiber, the retaining means being comprised of an elastic cloth strip, the fiber being sewn thereto in said sinuously looped disposition, means for applying a first optical signal into one end of the fiber, means for detecting a resulting optical signal from the other end of the fiber, means for comparing the first and resulting optical signals to obtain an indication of said movement, various loops of fiber having different radii, to produce variable sensitivity thereof with expansion or contraction of the sensor.

* * * * *